(12) United States Patent
Omegna De Souza Filho

(10) Patent No.: US 9,846,070 B2
(45) Date of Patent: Dec. 19, 2017

(54) MULTIPARAMETER DEVICE FOR MEASURING BY OPTICAL MEANS THE FILLING LEVEL OF TANKS AND RESERVOIRS OF LIQUIDS AND LIQUEFIED PRODUCTS, THE INDEX OF REFRACTION, AND FOR IMAGE ANALYSIS, WITHOUT MOVING PARTS

(71) Applicant: LUXTEC—SISTEMAS ÓPTICOS LTDA—ME, Campinas-SP (BR)

(72) Inventor: Cicero Livio Omegna De Souza Filho, Campinas-SP (BR)

(*) Notice: Subject to any disclaimer, the term of this patent is extended or adjusted under 35 U.S.C. 154(b) by 0 days.

(21) Appl. No.: 14/780,334

(22) PCT Filed: Mar. 19, 2014

(86) PCT No.: PCT/BR2014/000088
§ 371 (c)(1),
(2) Date: Jan. 4, 2016

(87) PCT Pub. No.: WO2014/153633
PCT Pub. Date: Oct. 2, 2014

(65) Prior Publication Data
US 2016/0116323 A1   Apr. 28, 2016

(30) Foreign Application Priority Data
Mar. 25, 2013 (BR) .......................... 1020130067946

(51) Int. Cl.
G01F 23/292 (2006.01)
G01N 21/41 (2006.01)

(52) U.S. Cl.
CPC ....... *G01F 23/292* (2013.01); *G01N 21/4133* (2013.01)

(58) Field of Classification Search
CPC .......................... G01F 23/292; G01N 21/4133
(Continued)

(56) References Cited

U.S. PATENT DOCUMENTS

| 3,995,168 A | 11/1976 | Neuscheler et al. |
| 4,287,427 A | 9/1981 | Scifres |

(Continued)

OTHER PUBLICATIONS

International Search Report in International Application No. PCT/BR2014/000088, Jun. 27, 2014, 2 pp.

*Primary Examiner* — Seung C Sohn
(74) *Attorney, Agent, or Firm* — Leydig, Voit & Mayer, Ltd.

(57) ABSTRACT

A new multiparameter device for measuring by optical means, the level of filling of tanks and reservoirs for liquids and liquefied products, index of refraction and image analysis, without moving parts, which is more specifically intended, but without restrictions of application, for the measuring the level of a liquid in a reservoir, besides being able to make possible the distinction and detection of the type of liquid included in this reservoir, by measuring the index of refraction and image analysis of these liquids, performing this task in a simple, practical and efficient manner through a specific configuration utilizing optical and electronic means, without use of moving parts, what allows that the same may be used for numerous applications between them, for the fuel quality control, the fuel identification, the measuring of the index of refraction, flow measurement, color measurement, temperature measurement and pressure measurement, inter alia, and more specifically for application in the automotive and associated industries.

12 Claims, 3 Drawing Sheets

(58) Field of Classification Search
USPC .......................................... 250/577, 227.22
See application file for complete search history.

(56) References Cited

U.S. PATENT DOCUMENTS

| | | | | |
|---|---|---|---|---|
| 4,354,180 | A | 10/1982 | Harding | |
| 4,994,682 | A | 2/1991 | Woodside | |
| 7,161,165 | B2 * | 1/2007 | Wirthlin | G01F 23/2922 |
| | | | | 250/577 |
| 7,710,567 | B1 * | 5/2010 | Mentzer | G01F 23/2924 |
| | | | | 250/577 |
| 7,719,690 | B2 * | 5/2010 | Childers | G01C 9/06 |
| | | | | 356/482 |
| 7,982,201 | B2 * | 7/2011 | Bryant | G01F 23/292 |
| | | | | 250/577 |

* cited by examiner

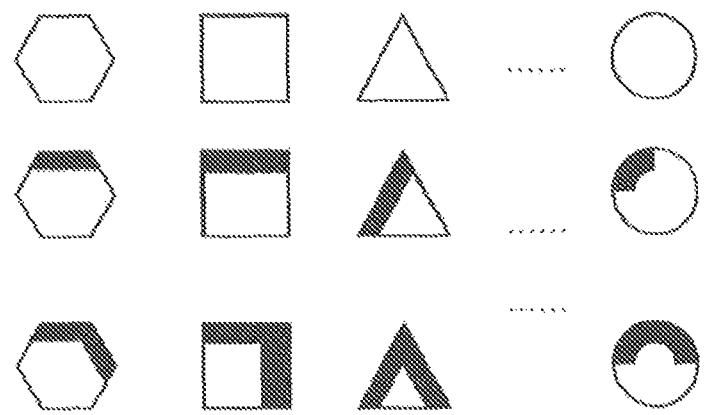
*Fig. 7*
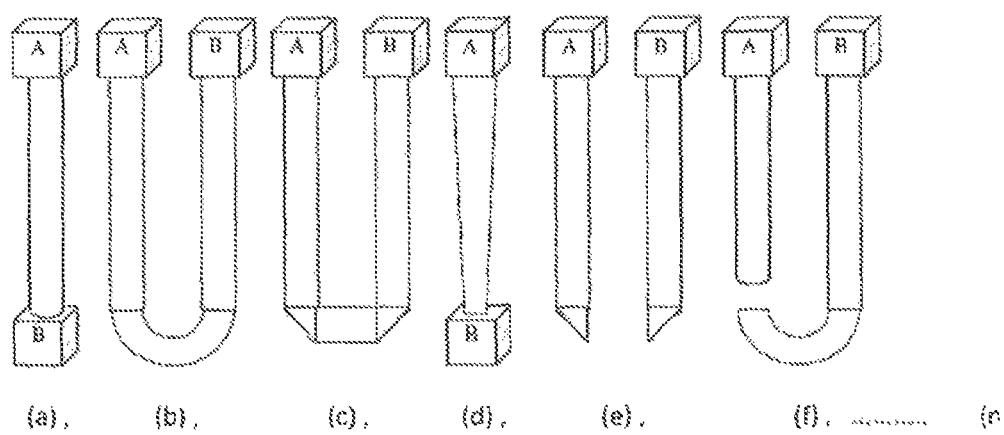
(a), (b), (c), (d), (e), (f), (g)
*Fig. 8*
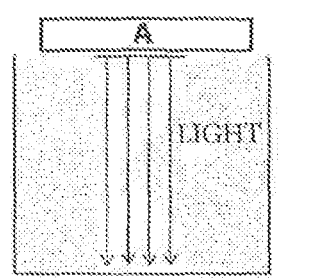 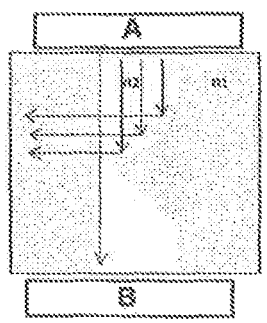 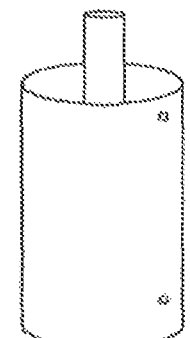
(a) (b)
*Fig. 9*    *Fig. 10*

MULTIPARAMETER DEVICE FOR MEASURING BY OPTICAL MEANS THE FILLING LEVEL OF TANKS AND RESERVOIRS OF LIQUIDS AND LIQUEFIED PRODUCTS, THE INDEX OF REFRACTION, AND FOR IMAGE ANALYSIS, WITHOUT MOVING PARTS

This report relates to the detailed description, accompanied of illustrative figures, of a new multiparameter device for measuring by optical means the filling level of tanks and reservoirs of liquids and liquefied products, the index of refraction, and for image analysis without moving parts, which is intended more specifically, but without application constraints, for measuring the level of a liquid in a reservoir, besides enabling the detection and distinction of the type of the liquid in the container by measuring the index of refraction and image analysis from the illumination of these liquids, performing this task in a simple, practical and efficient manner through a specific configuration by using optical and electronic means, without the use of moving parts. This allows that it can be used for numerous applications including, for quality control of fuels and liquids in general, for the identification of fuels and fuel mixtures by measuring index of refraction, flow measurement, color and pigmentation measurement, temperature measurement, pressure measurement among others, more specifically for applications in the chemistry, manufacturing and automotive industries and in related areas.

The measurement of the level of liquids can be carried out in many different ways, one using the wide range of technologies such as electronic, ultrasonic, magnetic, pneumatic, optical, and others, by means of specific devices which utilize such technologies. This can be proved by the large number of registered patents directly related to the theme. Physical phenomena such as Hall, Snell-Descartes, Evanescent field, Ultrasound effects, among others, have great potential for applicability, but may depend on sophisticated and expensive equipment and interpretation systems. The costs and the complexity of construction and configuration required for its proper functioning are important factors for the non-massive use of these devices.

Currently the majority of sensor and indicators devices of the amount of a liquid contained in a reservoir or tank, that do not use optical technologies, are characterized by assemblies composed of a floating element (float) attached to a rod changing the point of contact at a variable resistor according to the position of that float, which are moving parts constituent of variable resistance devices as a function of the displacement motion of a certain part, known as float. This variation of the electrical resistance proportional to the displacement of the float changes the current of the display indicating the level of the liquid stored within the tank or reservoir.

These designs have limitations such as, for example, the change in buoyancy by altering the float density, by absorbing the liquid portions or deformations, which changes its relative position. It can also be cited as other constraints: the degradation and alteration of the mass of the rod by chemical interactions between the liquid and the material from which it is made; its deformation by strikes or mechanical forces; the fact that the indication of the level is not linear in most cases; the fact that the value of the electrical resistance may vary with the wear caused by friction of contacts, etc. All these events or failures can lead to errors in reading.

Optical technology, by definition, can be regarded as one of the safest methods for measuring levels of classified liquids. A light source and a light sensitive converter can be installed outside of a tank or reservoir and the light path up to and/or within the reservoir may be defined by intrinsically safe optical components such as optical fibers, light guides, prisms, lenses, and others, shaping and directing the innocuous energy beam to the centre. The use of these features and components available in the market or not, allow the construction of devices for various applications in several fields of activities, and result in commercial products practical and simple to use.

These products allow the use of materials resistant to physical and chemical attacks provided that the optical properties inherent in the methodology and the presented principles are taken into account. Taking advantage of the energy of light, its image and projection, these products can replace many of measurement methods of liquids and liquefied products currently used with technical, economic and constructive advantages.

The present invention of a multiparameter device for measuring by optical means the filling level of tanks and reservoirs for liquid and liquefied products, index of refraction and image analysis, without moving parts, relates to one of such above mentioned products, which offers constructive and functional advantages over those already known in the art. Thus, the device presented in this report, is an innovative alternative that overcomes these shortcomings and has other unusual advantages, without compromising its production due to high cost or complexity of construction. Having modular construction and taking advantage of the properties of light, the sensor or sensor device presented here can measure besides the height of the column formed by the internal liquid to a reservoir, its index of refraction, its color, its flow, and other parameters. Jointly with an electronic processing, artificial neural networks, and other methodologies, it can structure a smart metering system suitable for the evaluation of a liquid or of a liquefied gas.

There are numerous patent documents that describe optical devices for measuring the level of a liquid for various applications and with various settings and operations, some devices with sophisticated and/or complicated constructions and technologies and others more simple, but none of these devices has the configuration, the disposition and the operation described in this patent, for a device for measuring by optical means the level of liquids and liquefied products in tanks and reservoirs by index of refraction and image analysis. Among these documents the following can be highlighted:

The patent document US2009039296, which describes a sensor device and includes at least one transparent elevation, which is formed on a surface. The transparent elevation is made of a first transparent material. At least a first facet of the transparent elevation defines a first angle with the surface. This first angle is greater than an angle at which a total reflection occurs at an interface between the first transparent material and air and is at the same time smaller than an angle at which a total reflection occurs at an interface between the first transparent material and the liquid. A light source is arranged to emit an incident beam in a first direction passing through the surface into the transparent elevation such that, in the presence of a liquid in first facet an incident ray will be transmitted through the first facet, wherein in the absence of a liquid the incident ray will be reflected due to a total reflection on the facets. Furthermore, a light detector is provided for detecting the reflected beam. Working in a similar way to a plate of an optical diffraction spectrometer;

The patent document U.S. Pat. No. 5,942,976, which describes a passive infrared intrusion detector for detecting radiation body, includes a tamper infrared detector, particularly for the detecting of spraying of the intrusion detector entrance window. The tamper detector includes a light source, a corresponding light sensor, and an optical diffraction grating structure outside the entry window. The light source and the light sensor may be in the same or opposite sides of the input window. For diffraction of first or higher order light, the light of the light source is focused onto the sensor, and a resulting electrical signal from the sensor is evaluated by an evaluation circuit. Where in the event of tampering, the effect of focusing of the optical diffraction grating structure is null, so that the light intensity at the detector is reduced. The drop in the light intensity triggers a tampering alarm signal;

The patent document U.S. Pat. No. 3,995,168, which describes a device for viewing from outside the level and the specific gravity of a liquid contained inside a tank, in particular flammable liquids, characterized by a plurality of light pipes paired with specific optical interface located in intervals therein within a holder with electrical means actuated by the energy of the light from one of the pair of light pipes thus to be conducted, due to the difference of the index of refraction caused by a lack of fuel in the optical interface zone to provide a visualization of the level of the fluid and/or the density of the fluid inside a tank;

The patent document U.S. Pat. No. 4,354,180 which describes an electro-optical probe designed for low liquid level, where a checking of self-supplying of the same is made with the means for interception of a portion of the light beam that reflects usually and constantly such portion that the electro-optical transducer receives to constantly generate a low level electrical signal even when the probe is wet. Where reinforcing means of the signal are provided to activate a failure alarm, which will be indicative of failure or malfunctioning of one or more elements of the system;

The patent document U.S. Pat. No. 4,287,427 which describes an apparatus for detecting the level of a liquid in a container, by modulating the intensity of the propagating light through an optical fiber light guide, a coating section having been removed or partially removed in it. The system consists of a light source which is coupled at the inlet end of a fiber, a fiber section from which the coating is removed, a vessel containing the liquid in which the bare fiber section can be immersed, and a detector at the outlet end of the fiber;

The patent document U.S. Pat. No. 4,443,699, which describes a level meter where a generated signal is passed through an elongated element of signal transport, preferably positioned perpendicular to the surface of a liquid whose level is to be measured. The signal is directed from the signal transport element to a detector element, which detects the output signal from the signal transport element. The signal output detected at an optical embodiment varies logarithmically with the depth of immersion of the signal carrying element into the fluid. A preferred embodiment uses an electromagnetic wave, such as, for example, light signal that passes through a light pipe element of signal transmission. For the index of refraction of the light pipe nearly corresponding with that of the fluid, a predetermined percentage of the wave is lost to the liquid every time that the light is reflected further along the tube. The part of the light detected at the detector, which is located in the place where the non-refracted light exits, is easily converted to an output that varies linearly with the depth in which the light signal component of the transport pipe is immersed in the fluid length.

In the Prior Art are found many other devices that use electro-optical technologies; however none of these devices have the advantages and the configuration characteristics and performance presented in this patent of multiparameter device for measuring by optical means the filling level of tanks and reservoirs of liquids and liquefied products, index of refraction, and image analysis without moving parts.

Next, references are made to figures that accompany this descriptive report, for its better understanding and illustration, where you see:

FIGS. 1a and 1b show a schematic flow diagram of a general configuration of the multiparameter device for measuring by optical means, which is essentially formed by: one light emitter (A), a light guide (C) of length "L", through which light is transmitted and a light detector (B).

FIG. 2 shows a schematic multiparameter device for measuring by optical means, object of the present invention, highlighting its general configuration details, conformation and functioning, where one can see the source or light emitter (A), the light detector (B), the image projector (D), the inflection points (E) with and without reflection and the light guide (C) being traversed by a light beam from the light emitter.

Figure 1:
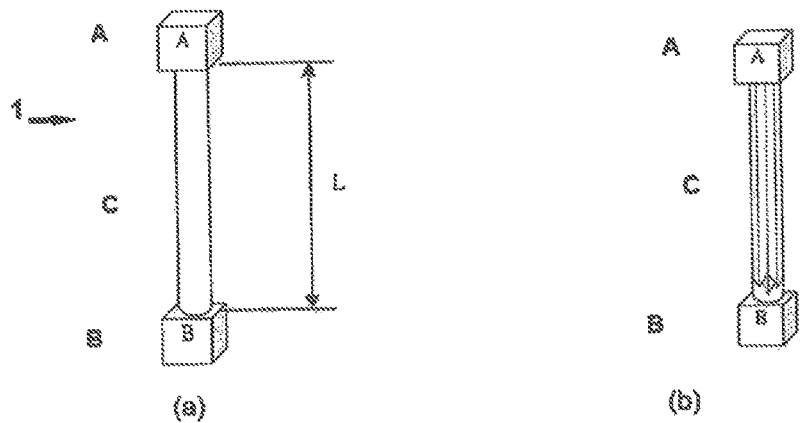
Figure 2:
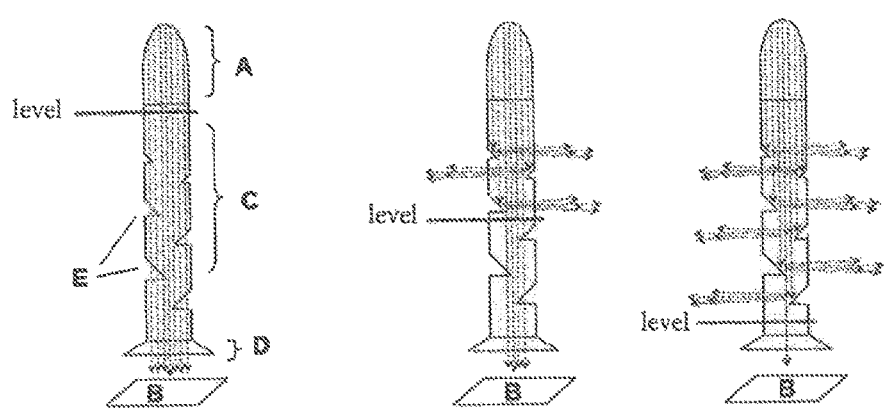
Figure 3:
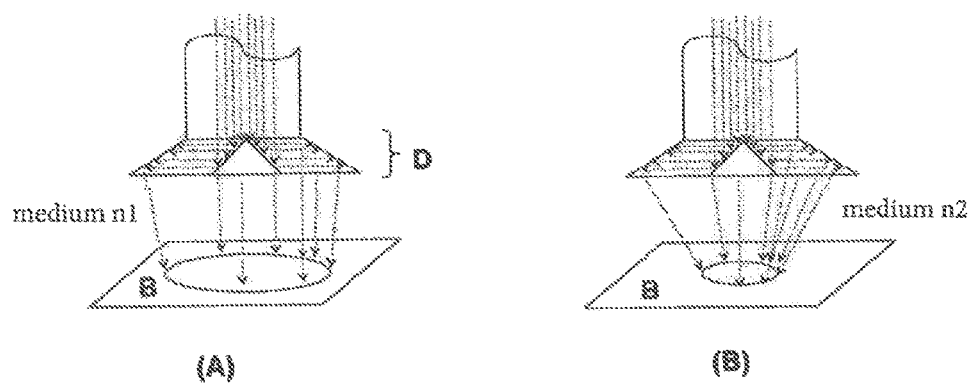
FIG. 3 shows in a schematically highlighted way the image projector (D) and the light detector (B) for the situation where the light is directed to the image sensor and to the light detector in an application with measuring of the index of refraction of the multiparameter device for measuring by optical means, object of this patent.
Figure 4:
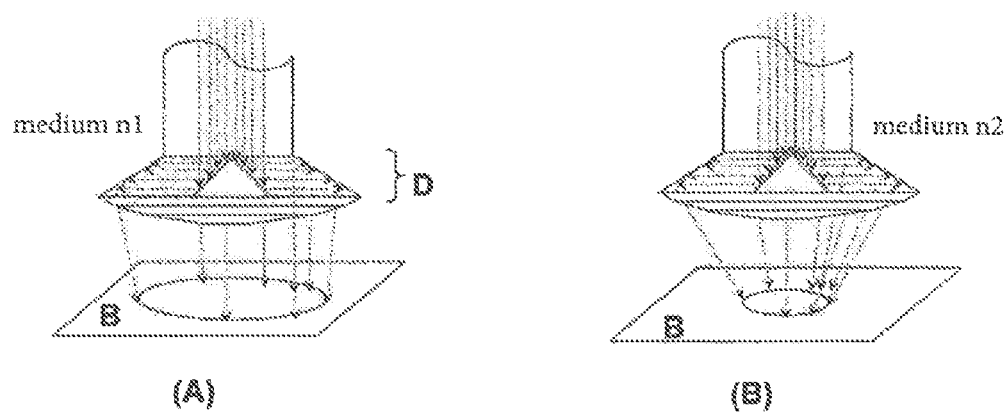
FIG. 4 shows in a schematically highlighted way the image projector (D) and the light detector (B) for the situation where the light is directed to the sensor of the image and to the light detector through different deviations in an application of the device for the multiparameter measuring by optical means, with measuring of the index of refraction.
Figure 5:
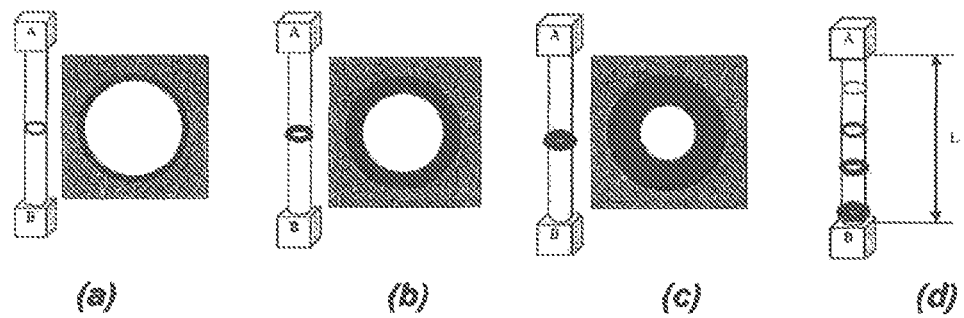

FIGS. 5 a, b, c and d, show a scheme of the combined effects on the detector image (B) when the introduction of four different circular inflection points arranged along the light guide of "L" length of the multiparameter device for measuring by optical means, with the same immersed in a medium of level lower than "L", represented by four different rings, such as images registered by the detector.

Figure 6:
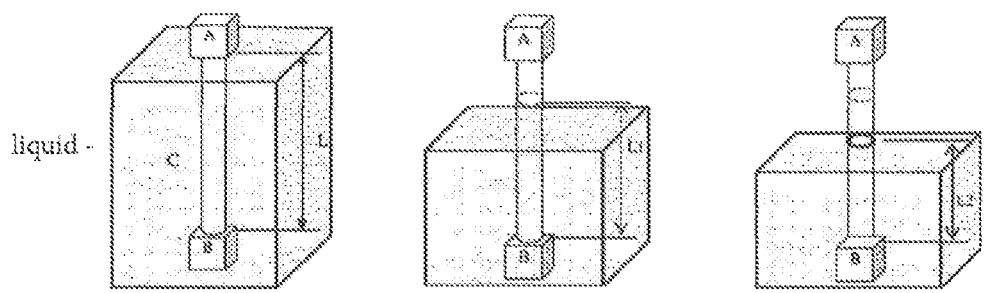

FIG. 6 shows schematically the operation of the multiparameter device for measuring by optical means, object of the present invention, when of the variation of the level of the liquid, exposing the points of inflection to the air successively until the complete withdrawal of the liquid from the device or until the complete removal of the liquid in which the device is immersed, whose image is shown in FIG. 5.

FIG. 7 shows some possible cross-sectional shapes of the multiparameter light guide device for measuring by optical means, not being limited to these, as well as some shapes and the influence of the inflection points that can vary from semicircles, sections of a crown, lines, freeform curves, conical, and other, according to the light guide device format.

FIG. 8 schematically represents the multiparameter device for measuring by optical means, object of the present invention, several possible versions of its final shape that may vary according to the desired function and application.

FIG. 9a shows schematically the operation of a turning point in the condition of the multiparameter device for measurement by optical means, in the situation in which the refractive indices of the internal and external medium of the light guide (n1 and n2) are nearby. The inflection point is set as a prism with the face on which the light falls at 45 degrees to the light guide shaft, highlighting the non-reflection of that light at the inflection point in the immersed position in the liquid medium. The angle of the face of the prism in relation to the light guide shaft can vary according to the application and to the refractive indices of the rod and of the sample liquid.

FIG. 9b illustrates schematically the operation of an inflection point in the condition of the multiparameter device for measuring by optical means in the situation in which the refractive indices of the internal and external media to the light guide (n1 and n2) are different, where the air/gas filled in the prism (air prism) entering as a prism with a face incident at 45 degrees or other suitable angle, as inflection point, highlighting the reflection of the inflection point in the condition of immersed in a gaseous medium.

FIG. 10 schematically represents a hysteresis chamber with communicating vessels, inner and outer, which can be used to prevent abrupt changes of the multiparameter device signal in the image sensor by the shaking of the liquid inside a tank in case of the movement of the same.

Next, is herein described a non-restrictive preferred embodiment of the present device, object of this patent, which configuration may vary in form suitable for each desired model and for each desired application; depicting one of the constructive possibilities which lead to realize the object described, and the form in which it works.

The multiparameter device for measuring by optical means, the filling level of tanks and reservoirs for liquids and liquefied products, index of refraction and imaging analysis without moving parts, object of the present invention, it is a measuring device (1) essentially formed by a light guide (C) having arranged at its ends, a light emitter or light power supply source (A), an optional image projector (D) and a light detector or photosensor (B) coupled to a specific image processor and/or register;

Where the light guide (C) abuts the light from a collimated parallel light beam, travelling its interior, while not allowing external interferences that may be composed of a bar or rod of any material transparent to the used light, whether it is visible or not, ultraviolet (UV) or infrared (IR), which may be image transmitting optical fiber; involved or not by layers of index of refraction materials for the occurrence of total internal reflection (RIT); and/or Involved or not by reflecting coatings; and/or with a surface layer of index of refraction (nd) smaller than core; wherein the light guide may have varied lengths (L) and formats, as well as their straight section, which can vary in the geometric shape required for the material used; with this rod, light guide, having inflection points, of defined light obstruction, arranged along the light guide length in strategic positions to their function with varying amounts of inflection points to different areas of obstruction of the light and location or having a gradual variation of the index of refraction throughout its structure;

Where the light guide (C) to prevent fogging and condensation of vapors and formation of liquid on its surface and having improved efficiency in measuring the image detected by the light detector (B) may or may not provide anti-fog/antifog coating, or heat utilization means generated by the light source for conducting the light guide serving as an electric anti-blurring means, or having a hydrophobic coating, or film-repellent liquid or a cooling/heating of the light guide or the hysteresis chamber where the control of the differences of temperature of the light guide and of the volumes of the medium around it, control the dew point.

Where the inflection points are characterized by being light incoming structures in angled guide faces according to the optical properties, of varying angles to the point of inflection and not necessarily constant, with typical optical properties described according to Snell-Descartes and other of reducing/restricting/deflecting light in the turning points related to the refringence of the medium in which they are immersed, acting as inverted prisms in relation to the light guide, inverted in relation to the light guide, optically composed by the medium or air in which they are immersed. The turning points are used to deflect the light according to the values of refractive indices of the light guide and of the medium in which it is located, whether liquid or air, through the properties related to the angle of incidence of the light at the interface of these media;

Where the points of inflection of the light guide may have a surface tension drain system, chiefly consisting of draining outlets drawn on the surface of the inflection points and or on the surface of the light guide, or use of angles and shapes that facilitate the flow of the liquid serving to prevent fluid buildup on the edges and cavities of the same.

Where the inflection points have the property of cancelling or not the light that fall on them, through reflection or refraction, altering and restricting in proportion to their area the total amount of light incident on the light detector, so that the alteration of the intensity of the light caused at the detector/receptor by an inflection point can be quantified. The inflection points must allow the gradual and controlled obstruction of the light along the light guide in such a way as to ensure that the detector recognizes such differences. The inflection points may vary in shape and influence/indentation of the same in the light guide. The shape of the inflection may be annular and/or vary to semicircles, sections of a crown, lines, freeform curves, conical, and/or other appropriate geometric shapes and adapted to the shape of the light guide.

Where the light transmitter (A) emitting a homogeneous and collimated beam of light toward the detector (B) through the light guide (C), a LED emitter, a laser transmitter, a OLED lamp, or other light source, that may be mono or multichromatic; and with these devices being powered by a specific source appropriate for each one of them.

Where the transmitter A can be replaced by an optical fiber that provides the light generated at another point to the light guide C.

Where the light detector (B) receives and detects the variation of the light and/or image as movement of the light beam or change in the position of the image on the detector that is proportional to the index of refraction of the medium and to the spectrum of light through a device of the photodetector type, may be a photocell, a photodiode, a photo transistor, a LDR (light dependent resistor), a photovoltaic cell, a photoconductive or an image detector, with the optional image capture projector (D), one CCD (charge coupled device) or a C-MOS chamber or other image capture device suitable for the application to which it is intended; directly or indirectly attached to a processor of images that can be of various types of operation such as by capacity and/or calculations; with the same connected and/or fed by a common or specific source to this light detector and that may be connected to image processing equipment and data as RNA Artificial Neural Network and others.

If the sensor is of the type LDR (Light Dependent Resistor) or circuit with photo sensor it can be connected to the level display with only two wires.

Where the optional image projector (D), providing the measuring of the index of refraction of the media, can be constituted by conical prism arranged in the center of the end portion of the light guide (C) adjacent to the light detector (B), where the light beam released from the inflection point is shifted to the sides of the light guide and then again reflected to a focal point in another prismatic face, depending on the index of refraction of the medium and of the angle to the incident light beam, where the light then will be refracted at the interface with the medium in which it is immersed, and finally directed to the photodetector.

The multiparameter device for measuring by optical means, the tanks filling level and for liquids and liquefied products, index of refraction and image analysis image, without moving parts, object of the present invention, through the optical properties of its settings and of the measuring the index of refraction, allows the evaluation of this parameter associated to the quality control of the means in which it is immersed, such as liquids, liquefied gas, fuels, and others; also permits evaluation of the color of the liquid, the measuring of the liquid flow between two points and other image analysis.

Accordingly, the associations for measuring different parameters or boundary conditions, can be made so as to obtain individual or multiple sensors as measurement of filling levels, of index of refraction, colorimeter, flow, diffraction and image that allow to quantify various practical measures in several industries, such as: quality control of fuels, fuels identification, measuring of index of refraction, fluid flow measuring, disturbance, bubble, foreign body introduced into the liquid medium, measuring of reservoir level, measuring, identification and characterization by the color, focusing of turning points images, use of optical corrections by optimization of the shapes of the sensor surfaces for specific focusing, temperature measurement, pressure measurement, color, image shape, edge definition, and diffraction.

The multiparameter device for measuring by optical means, the level of filling of tanks and reservoirs for liquid and liquefied products, index of refraction and image analysis, without moving parts, object of this patent, once formed and configured for a particular application can be placed within a hysteresis container in order to avoid abrupt variations in the signal of the same, caused by the swinging of the medium or liquid in which it is immersed in the event of movement of this medium or of the device-medium assembly, such as inside fuel tank of a vehicle. The hysteresis chamber may be of the type having a configuration of inner and outer communicating vessels which limit the passage of fluid therein.

From the above description of configuration and its concepts, one can establish the forms, functions and operational margins for the manufacturing of sensors of filling level, of index of refraction, of flow and of other measurements by the analysis of an image, which separately, isolated or not, together with various arrangements, are useful for measuring a parameter or multiparameter for application to liquids, liquefied gases or materials that satisfy the boundary conditions imposed for their use and of the optical properties and materials involved.

The multiparameter device for measuring by optical means, the filling level of tanks and reservoirs for liquid and liquefied products, index of refraction and image analysis, without moving parts, object of the present patent, has its operation based on the laws of the optics physics, easily understood by the explanation in the following sequence: where the light is projected in the inside of a stick/rod/light guide made of appropriate material from one end to the other. On the end opposite to the entry of the light or of light generating source is the photo sensor/photodetector/image processor. The light beam when moving towards the photodetector will find during this path, traps in the form of notches on the stick/rod/light guide, like prisms, hollow prisms at stick/rod/light guide, or cut-and-polished facets referred to as inflection points, these facets carved in this stick/rod/light guide, appropriately positioned, are intended to deflect the light of its path toward the photo sensor in function of the material that is filling it, liquid or gas/air. These facets then can be filled with air and/or with the gas of the volatilized liquid or they will be filled with the protagonist liquid in which the stick/rod/light guide is immersed. If it is filled with air/gas, the portion of the light beam that is focusing on this light will be shifted depending on the already demonstrated physical phenomena. If the prism is filled with the liquid, the light incident on the same will suffer refractions and will tend to follow the path toward the photodetector. The arrangement of the prisms/facets, as well as their sizes and shapes define the sensitivity and resolution of this meter. The shape of the facets should facilitate the draining of the liquid and will depend on characteristics of the product such as viscosity, surface tension, and others.

Under these conditions a small amount of light is intentionally released from the traps or turning points in its path and reaches the photodetector so as to point changes in its focus. This beam of light released from the traps, or inflection points, in this case in the center of the stick/rod/light guide is deflected in a conical prism to the sides of the stick/rod/light guide where by its turn the beam is again reflected to a focal point in another prismatic face. This reflection occurs at the interface due to a reflecting surface or by a total internal reflection (RIT) as a function of the index of refraction of the medium and of the angle of the face relative to the incident light beam. This light is then refracted at the interface with the medium in which it is immersed and the angle of this refraction varies according to the medium in which the device (stick/rod/light guide) is immersed and the angles of the interface of incidence of the light on the exit of the light directed to the photodetector. This photodetector is an image sensor such as a C-MOS chamber, CCD (charge coupled device) or other image capture device suitable for the application.

The walls of the prisms, or inflection points, may have multiple facets so as to allow that the light suffer different deviations with angles at this end according to the variation range of the index of refraction to be measured. Extrapolating the concept of hollow prism or air prism, or point of inflection as above described, introduced into a light guide, to different formats one may measure levels and other parameters through the effects that the different rates of refraction provide. Thus the shape, or final configuration of the herein proposed device, can vary depending on the desired function and application of the invention.

The multiparameter device for measuring by optical means, the tanks filling level for liquids and liquefied products, index of refraction and image analysis, without moving parts, object of this invention, can be manufactured with varied and significant amounts of turning points with different areas of obstruction and location. This imparts to this new type of sensor, a good resolution and the ability to be able to be devised to favor the linearization of the sensitivity curve of the light detector or other appropriate optical corrections according to some specific function.

In this manner, this multiparameter device for measuring by optical means, the level of filling of tanks and reservoirs for liquid and liquefied products, index of refraction and image analysis, without moving parts, which describes a device which is designed primarily to measure the liquid level in a reservoir, besides being able to make possible the detection and discrimination of the type of liquid included in this reservoir, through the measuring of the index of refraction and image analysis of these liquids, as above described, by introduction of various and appropriate turning points in a light guide, presents a configuration and a new, unique and novel solution of the optical technologies that will confer great advantages over optical or traditional devices of measuring of level of liquids and/or similar fluids currently used and found at this time in the market. Among these advantages can be mentioned: the fact of being modular with forms and functions, configurable and associative, compensating various forms of reservoirs; the fact that it allows for to compensate the response curve of the light transducer sensor into other signal facilitating the linearity or a suitable curve of easy interpretation of the measuring; the fact of measuring liquids, liquefied, rarefied or under pressure gases, as air/gases may be rarefied or under pressure; due to their simple and compact configuration and to the explosion proof composition materials; the fact of it not having moving parts exempts if from any mechanical wear. Further, one can mention functional advantages due to its manner of construction, as the fact of offering better quality and measuring accuracy when presented with anti-haze coating/antifog, being hydrophobic, presenting hysteresis tank, cooling/heating, having surface drain system, having flowing channels, thus enabling the quality control of fuels, making possible the identification of fuels and mixtures thereof, as well as allowing the measuring of index of refraction, the measuring of flow, the measuring of level, the measuring of color, enabling the focusing of the images of the inflection points, the measuring of temperature and the measuring of pressure, becoming a highly functional multiparameter device.

Thus, by the above described characteristics of configuration, application and operation, one can clearly note that the MULTIPARAMETER DEVICE FOR MEASURING BY OPTICAL MEANS, THE FILLING LEVEL OF TANKS AND RESERVOIRS FOR LIQUIDS AND LIQUEFIED PRODUCTS, INDEX OF REFRACTION AND IMAGE ANALYSIS, WITHOUT MOVING PARTS, is a new device to the Prior Art which is full of innovation conditions, inventive activity and unprecedented industrialization, which make it deserve the Privilege of Patent of Invention.

The invention claimed is:

1. A multiparameter device consisting of a measuring device essentially formed by a light guide, having arranged at its ends a light emitting source, an image projector and a photodetector/light and image sensor receptor coupled to an image processor and specific register; wherein the light guide abuts the light derived from a light beam, travelling its interior, not allowing external interferences and that may be composed of a bar or rod of a material transparent to the light used, and that may be image transmitting optic fiber, involved by layers of index of refraction material so that total internal reflection (RIT) occurs; involved by reflective coatings, with an index of refraction surface layer smaller than the core; wherein the light guide may have various lengths and straight formats, "U," "S," and "zig-zag" formats, as well as its straight section, which can vary in the geometric shape required for the material used; with this rod, light guide having inflection points of defined light obstruction, arranged along the light guide length in strategic positions to their function with varying amounts of inflection points with different light obstruction areas and location or having a gradual variation of the index of refraction throughout its structure.

2. The multiparameter device according to claim 1, including the light guide that may comprise anti-haze/antifog coating, as means of utilization of the heat generated by the light source conducting toward the light guide serving as a heat anti-fog, or presenting a hydrophobic coating or a liquid-repellent film, presenting a cooling/heating of the light guide rod and of the hysteresis chamber, where the control between the differences of light guide temperature and of media volumes located around it, control the dew point.

3. The multiparameter device according to claim 1, wherein the inflection points being light-guide incoming structures of angled surfaces according to the optical properties, of angles θ1° to θ2° for the point of inflection, not necessarily uniform, with typical optical properties described according to Snell-Descartes of reducing/restricting/deflecting light in the inflection points related to the refringence of the medium in which they are immersed, acting as inverted prisms relative to the light guide, facing the inside of the light guide optically composed by the medium or air in which they are immersed; wherein the turning inflection points being used to deflect light according to the values of indices of refraction of the light guide and of the medium in which it is located, whether liquid or gaseous, through the properties related to the angle of light incidence angle in the interface of these different media and may also include the reading of the difference between the gas and liquid phases in liquefied gases.

4. The multiparameter device according to claims 1 and 3, wherein the inflection points of the light guide are able to present a draining system also by surface tension, essentially composed of flow channels designed on the surface of the inflection points and in the surface of the light guide, and still by use of angles and shapes that facilitate the liquid flow in order to prevent fluid accumulation on the edges and cavities of the same.

5. The multiparameter device according to claims 1 and 3, wherein the inflection points have the property of deflecting the light that fall on them, through reflection or refraction, thereby altering and restraining in proportion to its area the total amount of light incident on the light detector, so that the alteration of light intensity caused in the detector/receptor by an inflection point can be quantified; and the inflection points must allow the gradual and controlled obstruction of the light along the light guide in such a way as to ensure that the detector recognizes these differences.

6. The multiparameter device according to claims 1 and 3, wherein the inflection points are able to vary in the shape and influence/entrance of the same in the light guide, where the form of the inflection points may be annular and vary to semicircles, sections of a crown, lines, freeform curves, tapered shapes and other geometric shapes appropriated and adapted to the light guide format.

7. The multiparameter device according to claim 1, wherein the light emitting source emits a light beam collimated toward the detector, through the light guide and it may be LED emitter emitting LASER, O-LED, lamp or other light source, and it may be monochromatic or multichromatic; and this light can be conducted to the light guide and also by an optical fiber, and through these devices being supplied by power source appropriate to the multiparameter device.

8. The multiparameter device according to claim 1, wherein the photodetector/light and image sensor receptor receives and detects the variation of the intensity of the light including as motion of the light beam or variation in the position of the image on the detector that is proportional to the index of refraction of the medium and to the spectrum of the light, through a device of the photodetector type, image detector, image capture sensor, a CCD (Charge Coupled Device), a C-MOS chamber or other image capture device suitable for the application for which it is intended; directly or indirectly attached to a images processor that can be of various operation types such as by capacity by calculations; with the same connected, being powered by common or specific source; with this light detector capable of being connected to image and data processing equipment with or without RNA Artificial Neural Network and others.

9. The multiparameter device according to claim 1, wherein the image projector performs the measurement of the index of refraction of the media, it may be constituted by a conical prism arranged in the center of the end portion of the light guide or other medium for reflection of the light, adjacent to the light detector, where the released light beam is shifted to the sides of the light guide and then again reflected to a focal point in other or in various prismatic faces, with several geometries that depending on the index of refraction of this medium and of the angle of this face or point of the curve relative to the incident light beam, the light will be refracted at the interface with the medium in which it is immersed, and finally directed to the image photodetector.

10. The multiparameter device according to claim 1, wherein the multiparameter device once it is constituted and configured for a particular application, is able to be placed inside a hysteresis tank avoiding abrupt variations of the signal of the same, caused by swinging the medium in which it is immersed, where the hysteresis reservoir may be comprised by a chamber with a configuration of internal and external communicating vessels.

11. The multiparameter device according to claims 8 and 9, wherein the image projector is capable of permitting the measuring of the speed and flow of the medium through disturbances caused in the image, and is capable of permitting the distinction of the color of the medium.

12. The multiparameter device according to claim 1, wherein the photodetector/light and image sensor receptor, which receives, identifies and quantifies the light beam possibly being a photocell, photodiode, photo-transistor, LDR (light dependent resistor), photovoltaic cell, photosensitive, or others, this light being mono or multichromatic: it may also be an image capture sensor, a CCD (charge coupled device), a C-MOS chamber or other image capture device suitable for the application to which it is intended.

\* \* \* \* \*